US011266836B2

(12) United States Patent
Charlesworth et al.

(10) Patent No.: US 11,266,836 B2
(45) Date of Patent: Mar. 8, 2022

(54) VARIABLE OPERATING POINT NEURAL ELECTROSTIMULATION SUCH AS TO TREAT RLS

(71) Applicant: Noctrix Health, Inc., San Francisco, CA (US)

(72) Inventors: Jonathan David Charlesworth, San Francisco, CA (US); Shriram Raghunathan, Castro Valley, CA (US)

(73) Assignee: NOCTRIX HEALTH, INC., San Francisco, CA (US)

( * ) Notice: Subject to any disclaimer, the term of this patent is extended or adjusted under 35 U.S.C. 154(b) by 0 days.

(21) Appl. No.: 17/241,924

(22) Filed: Apr. 27, 2021

(65) Prior Publication Data

US 2021/0260379 A1     Aug. 26, 2021

Related U.S. Application Data

(63) Continuation of application No. 17/062,010, filed on Oct. 2, 2020, now Pat. No. 11,103,691, and a
(Continued)

(51) Int. Cl.
*A61N 1/36* (2006.01)
*A61B 5/0531* (2021.01)
(Continued)

(52) U.S. Cl.
CPC ........ *A61N 1/36057* (2013.01); *A61B 5/0531* (2013.01); *A61B 5/4082* (2013.01);
(Continued)

(58) Field of Classification Search
CPC ............ A61N 1/36057; A61N 1/36034; A61N 1/36014; A61N 1/36; A61N 1/36139; A61N 1/36067; A61B 5/4836
(Continued)

(56) References Cited

U.S. PATENT DOCUMENTS

| 5,487,759 A | 1/1996 | Bastyr et al. |
| 5,725,471 A | 3/1998 | Davey et al. |

(Continued)

FOREIGN PATENT DOCUMENTS

| CN | 110603073 | 12/2019 |
| JP | 2020505099 | 2/2020 |

(Continued)

OTHER PUBLICATIONS

"International Application Serial No. PCT US2018 012631, Invitation to Pay Add'l Fees and Partial Search Report dated Mar. 27, 2018", 2 pgs.
(Continued)

*Primary Examiner* — Amanda K Hulbert
*Assistant Examiner* — Philip C Edwards
(74) *Attorney, Agent, or Firm* — Schwegman Lundberg & Woessner, P.A.

(57) ABSTRACT

Techniques to help improve efficiency or effectiveness of treating a disorder such as RLS or PLMD, such as by issuing neural electrostimulations to a particular patient, while varying one or more amplitude parameters (e.g., at least one of electrostimulation current amplitude, electrostimulation voltage amplitude, or electrostimulation pulsewidth duration). A corresponding patient-subjective or patient-objective response can be observed. A characteristic electrostimulation intensity relationship can be generated, for example, based on the determined respective at least one of RLS or PLMD response indication threshold amplitude parameters and the plurality of corresponding neural electrostimulation durations. Once this characteristic electrostimulation intensity relationship has been generated, it can then be used to control issuing subsequent neural electrostimulations to the particular patient according to (1) at least one goal and (2)
(Continued)

a variable operating point based upon the generated characteristic electrostimulation intensity relationship.

30 Claims, 5 Drawing Sheets

Related U.S. Application Data continuation of application No. PCT/US2020/054006, filed on Oct. 2, 2020, and a continuation of application No. 16/416,330, filed on May 20, 2019, which is a continuation of application No. 16/196,863, filed on Nov. 20, 2018, now Pat. No. 10,342,977, which is a continuation of application No. PCT/US2018/012631, filed on Jan. 5, 2018.

(60) Provisional application No. 63/015,758, filed on Apr. 27, 2020, provisional application No. 63/016,052, filed on Apr. 27, 2020, provisional application No. 62/910,241, filed on Oct. 3, 2019.

(51) Int. Cl.

| | | |
|---|---|---|
| *A61B 5/00* | (2006.01) | |
| *A61N 1/08* | (2006.01) | |
| *A61N 1/04* | (2006.01) | |
| *A61B 5/11* | (2006.01) | |
| *A61N 1/05* | (2006.01) | |
| *A61B 5/08* | (2006.01) | |
| *A61B 5/024* | (2006.01) | |

(52) U.S. Cl.
CPC .............. *A61B 5/4836* (2013.01); *A61N 1/08* (2013.01); *A61N 1/36* (2013.01); *A61N 1/36014* (2013.01); *A61N 1/3614* (2017.08); *A61N 1/3615* (2013.01); *A61N 1/36031* (2017.08); *A61N 1/36034* (2017.08); *A61N 1/36067* (2013.01); *A61N 1/36139* (2013.01); *A61N 1/36167* (2013.01); *A61B 5/0022* (2013.01); *A61B 5/02405* (2013.01); *A61B 5/08* (2013.01); *A61B 5/1114* (2013.01); *A61B 5/1116* (2013.01); *A61B 5/4809* (2013.01); *A61B 5/4815* (2013.01); *A61B 5/7264* (2013.01); *A61B 5/7475* (2013.01); *A61B 2562/0219* (2013.01); *A61N 1/0456* (2013.01); *A61N 1/0476* (2013.01); *A61N 1/0484* (2013.01); *A61N 1/0492* (2013.01); *A61N 1/0556* (2013.01); *A61N 1/36021* (2013.01); *A61N 1/36071* (2013.01); *A61N 1/36078* (2013.01); *A61N 2001/083* (2013.01)

(58) Field of Classification Search
USPC .......................................................... 607/46
See application file for complete search history.

(56) References Cited

U.S. PATENT DOCUMENTS

| | | | |
|---|---|---|---|
| 5,759,198 A | 6/1998 | Karell | |
| 5,995,873 A | 11/1999 | Rhodes | |
| 6,001,861 A | 12/1999 | Oertel et al. | |
| 6,114,326 A | 9/2000 | Schueler | |
| 6,507,757 B1 | 1/2003 | Swain | |
| 6,602,868 B2 | 8/2003 | McBrinn et al. | |
| 6,958,048 B2 | 10/2005 | Bonutti | |
| 7,403,821 B2 | 7/2008 | Haugland et al. | |
| 7,774,068 B1 | 8/2010 | Lozano | |
| 7,783,348 B2 | 8/2010 | Gill et al. | |
| 8,145,317 B2 | 3/2012 | Demarais et al. | |
| 8,365,741 B2 | 2/2013 | Hennings et al. | |
| 8,938,303 B1 | 1/2015 | Matsen | |
| 8,983,617 B2 | 3/2015 | Chavan et al. | |
| 9,002,477 B2 | 4/2015 | Burnett | |
| 9,017,273 B2 | 4/2015 | Burbank et al. | |
| 9,205,264 B2 | 12/2015 | Heruth et al. | |
| 9,302,046 B1 | 4/2016 | Giuffrida et al. | |
| 9,327,121 B2 | 5/2016 | Thacker et al. | |
| 9,387,338 B2 | 7/2016 | Burnett | |
| 9,452,287 B2 | 9/2016 | Rosenbluth et al. | |
| 9,474,898 B2 | 10/2016 | Gozani et al. | |
| 9,504,827 B2 | 11/2016 | DeGiorgio et al. | |
| 9,561,371 B2 | 2/2017 | Elborno | |
| 9,566,470 B2 | 2/2017 | Malizia | |
| 9,604,056 B2 | 3/2017 | Starr et al. | |
| 9,610,448 B2 | 4/2017 | Hou et al. | |
| 9,656,070 B2 | 5/2017 | Gozani et al. | |
| 9,662,491 B2 | 5/2017 | Yonce et al. | |
| 9,662,502 B2 | 5/2017 | Giuffrida et al. | |
| 9,694,181 B2 | 7/2017 | Bhadra et al. | |
| 9,713,711 B2 | 7/2017 | Hershey et al. | |
| 9,737,709 B2 | 8/2017 | Bachinski et al. | |
| 9,750,933 B2 | 9/2017 | Gregory et al. | |
| 9,802,039 B2 | 10/2017 | Palermo et al. | |
| 9,802,041 B2 | 10/2017 | Wong et al. | |
| 9,808,620 B2 | 11/2017 | Kent | |
| 9,808,627 B2 | 11/2017 | Gliner et al. | |
| 9,814,880 B2 | 11/2017 | Hershey et al. | |
| 10,195,425 B2 | 2/2019 | Ostroff et al. | |
| 10,342,977 B2 | 7/2019 | Raghunathan | |
| 11,103,691 B2 | 8/2021 | Charlesworth et al. | |
| 2003/0176822 A1 | 9/2003 | Morgenlander | |
| 2004/0093093 A1 | 5/2004 | Andrews | |
| 2006/0069415 A1 | 3/2006 | Cameron et al. | |
| 2006/0173074 A1 | 8/2006 | Ellmen et al. | |
| 2008/0262053 A1 | 10/2008 | Reess | |
| 2009/0062685 A1 | 3/2009 | Bergethon et al. | |
| 2009/0221943 A1 | 9/2009 | Burbank et al. | |
| 2010/0049111 A1 | 2/2010 | Sorg | |
| 2010/0160712 A1 | 6/2010 | Burnett et al. | |
| 2010/0191311 A1 | 7/2010 | Scheiner et al. | |
| 2010/0249637 A1 | 9/2010 | Walter et al. | |
| 2011/0054573 A1 | 3/2011 | Mitchell | |
| 2012/0101358 A1 | 4/2012 | Boettcher et al. | |
| 2013/0245486 A1* | 9/2013 | Simon .................. | A61B 5/4041 600/546 |
| 2013/0325084 A1 | 12/2013 | Lee | |
| 2014/0148725 A1 | 5/2014 | Cadwell | |
| 2015/0066105 A1 | 3/2015 | Elborno | |
| 2015/0174002 A1 | 6/2015 | Burbank et al. | |
| 2015/0272815 A1 | 10/2015 | Kitchens | |
| 2016/0030280 A1 | 2/2016 | Jones | |
| 2016/0158542 A1 | 6/2016 | Ahmed | |
| 2016/0310741 A1 | 10/2016 | Baru et al. | |
| 2016/0354604 A1 | 12/2016 | Kent | |
| 2017/0157398 A1 | 6/2017 | Wong et al. | |
| 2017/0157404 A1 | 6/2017 | Moffitt et al. | |
| 2017/0216586 A1 | 8/2017 | Kent | |
| 2017/0266443 A1 | 9/2017 | Rajguru et al. | |
| 2019/0001129 A1 | 1/2019 | Rosenbluth et al. | |
| 2019/0083784 A1 | 3/2019 | Raghunathan | |
| 2020/0108251 A1 | 4/2020 | Raghunathan | |
| 2021/0100998 A1 | 4/2021 | Charlesworth et al. | |

FOREIGN PATENT DOCUMENTS

| | | |
|---|---|---|
| WO | 2015109023 | 7/2015 |
| WO | 2017023864 | 2/2017 |
| WO | 2018129351 | 7/2018 |
| WO | WO2018/129351 | 7/2018 |
| WO | 2021067751 | 4/2021 |

OTHER PUBLICATIONS

"International Application Serial No. PCT US2018 012631, International Search Report dated May 30, 2018", 5 pgs.
"International Application Serial No. PCT US2018 012631, Written Opinion dated May 30, 2018", 8 pgs.

(56) References Cited

OTHER PUBLICATIONS

"U.S. Appl. No. 16/196,863, Notice of Allowance dated Feb. 20, 2019", 8 pgs.

"International Application Serial No. PCT US2018 012631, International Preliminary Report on Patentability dated Jul. 18, 2019", 10 pgs.

"Chinese Application Serial No. 201880012637.9, Notification to Make Rectification dated Sep. 10, 2019", w o English Translation, 1 pg.

"U.S. Appl. No. 16/416,330, Preliminary Amendment filed Dec. 26, 2019", 8 pgs.

"European Application Serial No. 18736570.5, Extended European Search Report dated Sep. 30, 2020", 7 pgs.

"International Application Serial No. PCT US2020 054006, International Search Report dated Dec. 21, 2020", 7 pgs.

"International Application Serial No. PCT US2020 054006, Written Opinion dated Dec. 21, 2020", 8 pgs.

"U.S. Appl. No. 17/062,010, Non Final Office Action dated Jan. 7, 2021", 11 pgs.

"Personalized medicine", https: web.archive.org web 20190417064230 https: www.nature.com subjects personalized-medicine, (Apr. 17, 2019), 5 pgs.

"National Institutes of Health", https: web.archive.org web 20190829044030 https: allofus.nih.gov, (Aug. 29, 2019), 6 pgs.

"U.S. Appl. No. 17/062,010, Response filed Apr. 7, 2021 to Non Final Office Action dated Jan. 7, 2021", 14 pgs.

"U.S. Appl. No. 16/416,330, Non Final Office Action dated Apr. 14, 2021", 7 pgs.

"U.S. Appl. No. 17/062,010, Notice of Allowance dated Apr. 23, 2021", 5 pgs.

"U.S. Appl. No. 17/062,010, PTO Response to Rule 312 Communication dated May 20, 2021", 2 pgs.

Allen, R P, "Restless Legs Syndrome Willis-Eckbom Disease Pathophysiology", Sleep Med Clin. , 10(3), (2015), 207-214.

Clemens, S, "Restless leg syndrome: revisiting the dopamine hypothesis from the spinal cord perspective", Neurology, 67, (2006), 7 pgs.

Hayashibe, Mitsuhiro, "Evoked Electromyographically Controlled Electrical Stimulation", Frontiers in Neuroscience, (Jul. 14, 2016), 7 pgs.

Kilgore, K. L, "Nerve conduction block utilising high-frequency alternating current.", Med Biol Eng Comput., 42(3), (May 2004), 394-406.

Mitchell, U, "Medical devices for restless leg syndrome—clinical utility of the Relaxis pad", Ther and Clin Risk Management, (2015), 1789-1794.

Qing, K, "Burst-Modulated Waveforms Optimize Electrical Stimuli for Charge Efficiency and Fiber Selectivity", IEEE Trans Neural Syst Rehabil Eng 23(6), (Nov. 2015), pp. 936-945.

Schoen, Nathan, "The Use of Intraoperative Electromyogram During Spinal Cord Stimulator Placement Surgery: A Case Series", World Neurosurgeryvol. 100, (Apr. 2017), pp. 74-84.

Stewart, W, "Prevalence and burden of overactive bladder in the United States", World J Urol, 20 327-336, (2003), 11 pgs.

Vance, Carol GT, "Using TENS for pain control: the state of the evidence", Pain Management 4(3), 197-209, (2014), 13 pgs.

U.S. Appl. No. 16/196,863 U.S. Pat. No. 10,342,977, filed Nov. 20, 2018, Restless Leg Syndrome or Overactive Nerve Treatment.

U.S. Appl. No. 16/416,330, filed May 20, 2019, Restless Leg Syndrome or Overactive Nerve Treatment.

U.S. Appl. No. 17/062,010, filed Oct. 2, 2020, Peripheral Nerve Stimulation for Restless Legs Syndrome.

"U.S. Appl. No. 16/416,330, Notice of Allowance dated Aug. 27, 2021", 5 pgs.

"U.S. Appl. No. 16/416,330, Response filed Jul. 14, 2021 to Non Final Office Action dated Apr. 14, 2021", 9 pgs.

\* cited by examiner

VARIABLE OPERATING POINT NEURAL ELECTROSTIMULATION SUCH AS TO TREAT RLS

CLAIM OF PRIORITY

This patent application claims the benefit of priority of:
(1) Charlesworth U.S. Provisional Patent Application Ser. No. 63/016,052, NEUROSTIMULATION WAVEFORM MODULATION SUCH AS TO TREAT RLS, filed on Apr. 27, 2020;
(2) Raghunathan PCT Patent Application Number PCT/US2018/012631, RESTLESS LEG SYNDROME OR OVERACTIVE NERVE TREATMENT, filed on Jan. 5, 2018;
(3) Raghunathan U.S. patent application Ser. No. 16/196,863, RESTLESS LEG SYNDROME OR OVERACTIVE NERVE TREATMENT, filed on Nov. 20, 2018, which issued on Jul. 9, 2019 as U.S. Pat. No. 10,342,977;
(4) Raghunathan U.S. patent application Ser. No. 16/416,330, RESTLESS LEG SYNDROME OR OVERACTIVE NERVE TREATMENT, filed on May 20, 2019;
(5) Charlesworth et al. U.S. Provisional Patent Application Ser. No. 62/910,241, PERSONALIZED SCREENING OR TUNING FOR NERVE STIMULATION, filed on Oct. 3, 2019;
(6) Charlesworth et al. U.S. patent application Ser. No. 17/062,010, PERIPHERAL NERVE STIMULATION FOR RESTLESS LEGS SYNDROME, filed on Oct. 2, 2020;
(7) Charlesworth et al. PCT Patent Application Number PCT/US2020/054006, PERIPHERAL NERVE STIMULATION FOR RESTLESS LEGS SYNDROME, filed on Oct. 2, 2020; and
(8) Raghunathan et al. U.S. Provisional Patent Application Ser. No. 63/015,758, SYSTEMS AND METHODS FOR TREATMENT OF FOCAL DYSTONIA OR OVERACTIVE NERVES, filed on Apr. 27, 2020
the benefit of priority of each of which is claimed hereby, and each of which is incorporated by reference herein in its entirety.

CROSS-REFERENCE TO RELATED PATENT DOCUMENTS

This patent application is also related to:
(1) Raghunathan U.S. Provisional Patent Application Ser. No. 62/442,798, METHODS TO TREAT SYMPTOMS FROM OVERACTIVITY OF NERVES, filed on Jan. 5, 2017; and
(2) Raghunathan U.S. Provisional Patent Application Ser. No. 62/552,690, SYSTEMS METHODS AND DEVICES TO MODULATE NERVE ACTIVITY TO TREAT NEUROLOGICAL DISORDER AND IMPROVE SLEEP QUALITY, filed Aug. 31, 2017;
each of which is incorporated by reference herein in its entirety.

TECHNICAL FIELD

This document pertains generally, but not by way of limitation, to neural electrostimulation and, more particularly, but not by way of limitation, to variable operating point neural electrostimulation, such as to treat Restless Legs Syndrome (RLS) or Periodic Limb Movement Disorder (PLMD).

BACKGROUND

Electrical nerve stimulation can be used to treat one or more conditions, such as chronic or acute pain, epilepsy, depression, bladder disorders, or inflammatory disorders. There can be significant variability in the efficacy of the electrical nerve stimulation signal in activating the target nerve, particularly when the stimulation signal is delivered transcutaneously (e.g., applied externally to the skin to a neural target within or under the skin), and in recruiting particular nerve fibers to achieve a desired effect. Establishing safe and reliable nerve recruitment can thus be challenging, and treatment of a particular disorder may depend upon the nerve type (e.g., with central or peripheral nervous system), function (e.g., motor or sensory) and specific fibers (e.g., A-$\alpha$, A-$\beta$, A-$\lambda$, B, or C fibers) to be activated.

Certain neurological disorders can be attributed to overactivity of sensory or other peripheral nerve fibers which can disrupt quality of life, and/or the processing of such neural activity in the brain. Restless Legs Syndrome (RLS) and Periodic Limb/Leg Movement Disorder (PLMD) are two such neurological conditions that can significantly affect sleep in human patients. RLS (which can also be called Willis-Ekbom Disease (WED)) patients can experience uncomfortable tingling sensations in their lower limbs (legs) and, less frequently in the upper limbs (arms). RLS is characterized by an uncontrollable urge to move the affected limb(s). Such sensations can often be temporarily relieved by moving the limb voluntarily, but doing so can interfere with the RLS patient's ability to fall asleep. PLMD patients can experience spontaneous movements of the lower legs during periods of sleep, which can cause the PLMD patient to wake up.

Moderate to severe RLS can be a debilitating sleep disorder. Many RLS patients become refractory to the leading RLS medications yet have few alternatives. For a patient diagnosed with primary RLS (e.g., not secondary to some other primary co-morbidity, such as diabetes, neuropathy, etc.), the first line of treatment may involve one or more of behavior changes, sleep changes, or exercise. The second line of treatment may involve dopaminergic therapy or iron level management, or both. Dopaminergic therapy frequently leads to tolerance of the drug (termed augmentation), such that RLS patients must increase the dosage over time. Even under the highest safe dosages, efficacy of dopaminergic therapy declines significantly. The third line of treatment may involve one or more of anti-convulsants, off-label opioids, or benzodiazepines. The pharmaceutical therapies that are frequently part of current treatments for RLS patients can have serious side-effects, which may include progressively worsening RLS symptoms. There have been case reports of improvement in RLS symptoms for patients with having implanted spinal cord stimulation (SCS) therapy for pain. However, the use of implanted medical devices presents significant additional risks to patient health, are unproven, and are very expensive—and thus are not part of the standard of care.

SUMMARY

The present inventor has recognized, among other things, that there are technical problems to be solved in during a session of transcutaneous neural electrostimulation (also referred to herein as "neurostimulation") to treat Restless Legs Syndrome (RLS). During a session of transcutaneous neurostimulation to treat Restless Legs Syndrome (RLS), the following characteristics of the neurostimulation system have been recognized by the present inventor to be advantageous. First, the transcutaneous neurostimulation system should induce consistent subjective perceptual sensations by the patient, such as to make possible and enhance relaxation and sleep. Variation in subjective perceptual sensations by the patient are likely to be alerting in nature, such as to promote psychological or physiological arousal or both, and may thus interfere with sleep, such as during and shortly after applying the neurostimulation. Such variation in subjective perceptual sensations can be undesirable for treating a sleep disorder such as RLS. Second, the transcutaneous neurostimulation system should maintain consistent therapeutic relief. Assuming that neurostimulation induces relief by modulating neural circuitry, the system should maintain that modulation at a level sufficient to maintain therapeutic relief. However, maintaining such consistency in subjective perceptual sensations by the patient can be challenging, such as for one or more reasons. First, high amounts of electrical power are needed to generate consistently high neurostimulation stimulation waveform amplitudes over long durations (e.g., >30 minutes) of neural electrostimulation. This is especially a concern for wearable neural electrostimulation devices, since higher power involves more energy storage in larger batteries, larger circuit components, and higher power operation can lead to uncomfortably high device operating temperature in contact with the skin of the patient. Second, impedance in the electrode-skin interface can increase such as due to variation in the skin or electrode, thus using higher power to generate a constant current of neurostimulation. This is especially a concern when hydrogel electrodes are re-used for multiple or numerous sessions; in this case, the electrode surface may become dehydrated or may become (partially) covered in dead skin cells, thus increasing electrode-skin interface impedance. In cases of limited stimulation voltage or power, such increased electrode-skin impedance may inhibit or prevent the system from providing and maintaining a constant current of neurostimulation. Third, biological neural circuits can adapt or habituate to neurostimulation. This can happen through one or more mechanisms such as can include "neural accommodation" and "neural plasticity." Unaccounted for, such adaptation can mean that progressively higher neural electrostimulation power is needed to induce the same extent of physiological mechanistic effect that leads to providing therapeutic relief.

As explained in more detail below, the present techniques can help improve efficiency or effectiveness of treating a disorder such as RLS or PLMD, such as by generating and delivering neural electrostimulation therapy signals to a particular patient, while varying at least one amplitude parameter (e.g., at least one of electrostimulation current amplitude, electrostimulation voltage amplitude) and at least one timing parameter (e.g., pulsewidth, interpulse interval, pulse repetition frequency, pulse shape) that together define a stimulation intensity for a particular electrostimulation therapy signal. A corresponding patient-subjective or patient-objective response can be observed. A characteristic electrostimulation intensity relationship can be generated, for example, based on the determined respective at least one of an RLS or PLMD response indication threshold for a given amplitude parameter across a plurality of values of one of the at least one timing parameter (e.g., pulsewidth). Once this characteristic electrostimulation intensity relationship has been generated, it can then be used to control issuing subsequent neural electrostimulations to the particular patient according to (1) at least one goal and (2) a variable operating point based upon the generated characteristic electrostimulation intensity relationship.

Each of these non-limiting examples described herein can stand on its own, or can be combined in various permutations or combinations with one or more of the other examples. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
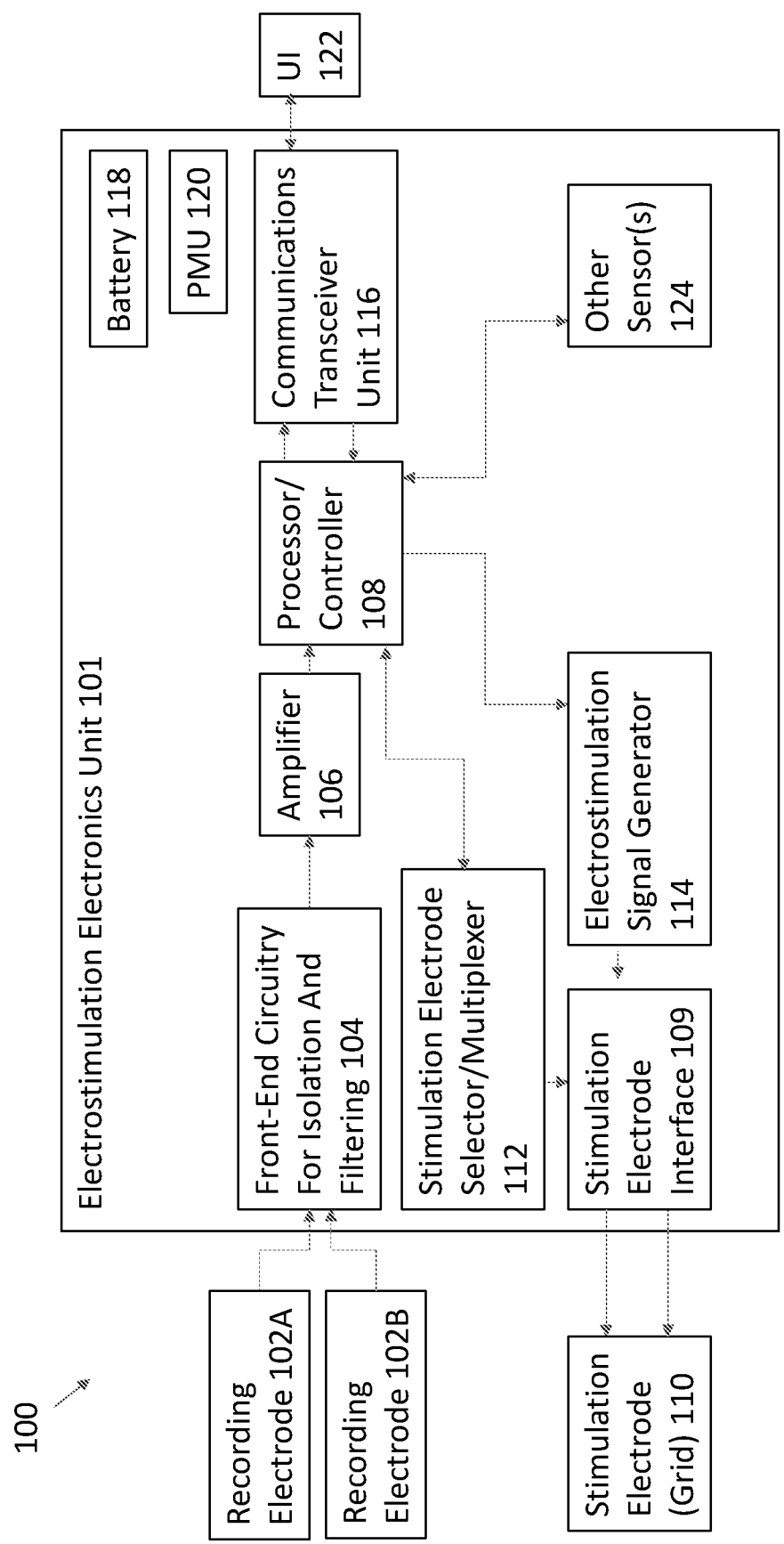
FIG. 1 shows an example of an architecture of portions of a system for treating a particular patient, such as a particular patient having one or more symptoms associated with at least one of Restless Legs Syndrome (RLS) or Periodic Limb Movement Disorder (PLMD).

As explained in more detail below, the present techniques can help improve efficiency or effectiveness of treating a disorder such as RLS or PLMD, such as by issuing neural electrostimulations to a particular patient, while varying one or more amplitude parameters (e.g., at least one of electrostimulation current amplitude, electrostimulation voltage amplitude, or electrostimulation pulsewidth duration). A corresponding patient-subjective or patient-objective response can be observed. A characteristic electrostimulation intensity relationship can be generated, for example, based on the determined respective at least one of RLS or PLMD response indication threshold amplitude parameters and the plurality of corresponding neural electrostimulation durations. Once this characteristic electrostimulation intensity relationship has been generated, it can then be used to control issuing subsequent neural electrostimulations to the particular patient according to (1) at least one goal and (2) a variable operating point based upon the generated characteristic electrostimulation intensity relationship.

As used herein, "sensory threshold" refers to the lowest stimulation level (as expressed in a particular combination of electrostimulation parameters defining a pulsed electrical signal, e.g., pulse current, pulse width, pulse waveform, etc.) at which a pulsed electrostimulation signal is perceptible to a patient receiving the electrostimulation signal.

The term "tonic muscle activation" refers to an isometric muscle contraction or similar muscle activation that is sustained and consistent over time and does not induce periodic leg movements (e.g., clonic or jerking movements occurring at a rate exceeding once per minute). When measured by a surface electromyogram (SEMG) sensed from the skin of the patient above the activated muscle, the SEMG activity induced by the tonic activation is characterized by consistently elevated amplitude over baseline with no significant short-lived changes in amplitude. The increase in muscle tone may (or may not) be noticeable to the patient or an observer, but there are no noticeable rapid movements or jerks.

The term "phasic muscle activation" refers to activation that induces period leg movements that are noticeable to the patient or an observer and which occur at least once per minute. Movements associated with phasic muscle activation may appear as a twitch, kick, or jerk, and the associated SEMG signal is characterized by large, abrupt, short-lived (e.g., <1 second) changes in amplitude.

The term "tonic motor threshold" refers to the lowest stimulation level (as expressed by a particular combination of electrostimulation parameters defining a pulsed electrostimulation signal, e.g., current, pulse width, pulse waveform, etc.) at which a pulsed electrostimulation signal causes specifically tonic muscle activation (as opposed to no muscle activation, phasic muscle activation, or a combination of tonic and phasic muscle activation), such that decreasing one of the parameters defining the pulsed electrostimulation signal would result in no tonic muscle activation of the muscle innervated by the electrostimulation signal. If there is no stimulation level that generates tonic muscle activation in the absence of phasic muscle activation, then the tonic motor threshold is undefined.

The term "distraction threshold" refers to the highest electrostimulation level (as expressed by a particular combination of electrostimulation parameters) that is comfortable, non-distracting, and compatible with a particular activity. For example, a sleep distraction threshold refers to the highest stimulation level that is comfortable, non-distracting, and compatible with sleep, such that increasing one of the parameters defining the sleep distraction threshold would result in a stimulation level that is incompatible with sleep. The sleep distraction threshold may be established by one or more of 1) the patient's subjective opinion (e.g., while awake and receiving an electrostimulation test signal); 2) an adverse effect on the patient's sleep while receiving an electrostimulation signal compared to no signal, such as A) an increase in sleep onset latency (i.e., time needed for the patient to fall asleep), B) an increase in sleep fragmentation as determined by one or more body parameters such as sleep movement, EEG signals, heart rate signals, etc., C) a decrease in sleep efficiency, D) a decrease in total sleep time, or E) an increase in wakefulness or arousal episodes after sleep onset. Other distraction thresholds (for example, working distraction threshold) may also be identified by testing a patient while the patient has the particular activity in mind or is performing the activity.

The term "tolerability threshold" refers to the highest stimulation level (as expressed by a particular combination of electrostimulation parameters) that a patient could tolerate for a period of one minute, in the patient's subjective opinion. The tolerability threshold refers to a level of stimulation that the patient experiences as distracting or uncomfortable, but which may be tolerated for a short period of time and is not painful.

The term "pain threshold" refers to the minimum stimulation level (as expressed by a particular combination of electrostimulation parameters) that the patient experiences as painful.

The term "electrostimulation test signal" (ETS) refers to a pulsed electrostimulation signal defined by a plurality of parameters (e.g., pulse current, pulse width, pulse waveform, etc.) that is applied to a body location proximate to a target nerve structure (e.g., a peroneal, sural, or femoral nerve or branch thereof) for the purpose of determining a patient-subjective or patient-objective patient response to the ETS.

FIG. 1 shows an example of an architecture of portions of a system 100 for treating a particular patient, such as a particular patient having one or more symptoms associated with at least one of Restless Legs Syndrome (RLS) or Periodic Limb Movement Disorder (PLMD). The present techniques can include using external transcutaneous neural electrostimulation applied via at least one electrostimulation electrode 110A . . . 110N. The electrostimulation electrodes 110A . . . 110N can be configured for location at a first external target body location. Such external electrostimulation electrodes 110A . . . 110N can be part of an external electrostimulation electrode grid 110. The electrostimulation electrode grid 110 can include a number (e.g., 2, 3, 4, 5, 6, 7, 8, 9, or even more) of selectable electrostimulation electrodes 110A . . . 110N. The electrostimulation electrode grid 110 can be carried and placed into location by a wearable elastic or other band or sleeve (e.g., like a knee brace). The carrier can allow the electrodes 110A . . . 110N to be placed against the patient's skin, such as at a location above or superficial to the patient's common peroneal nerve.

An electrostimulation electronics unit 101 can be coupled to the stimulation electrode grid 110, such as for transcutaneously delivering high frequency electrical nerve stimulation, such as to an external location superficial to the peroneal nerve of the patient. The electrostimulation electronics unit 101 can include on-board circuitry. The on-board circuitry can include electrostimulation electrode interface circuitry, such as stimulation electrode selector/multiplexor 112 circuitry. The stimulation electrode selector/multiplexor 112 can be used to select or adjust one or more or a combination of particular electrodes 110A . . . 110N for delivering neural electrostimulations to the patient. The stimulation electrode selector/multiplexor 112 can be coupled to an electrostimulation signal generator 114, such as can be controlled by processor or controller circuitry 108. In an example, the electrostimulation signal generator 114 can include its own separate microcontroller, a Field-Programmable Gate Array (FPGA), or other suitable circuitry that can be separate from the processor or controller 108, which may likewise include one or more microcontrollers, FPGAs, or other processing elements. In various embodiments, the electrostimulation generator 114 and controller 108 may together or separately comprise one or more hardware elements executing programmable code, e.g., software, firmware, or other code.

Sensing or recording electrodes 102 can be coupled to the electrostimulation electronics unit 101. The sensing or recording electrodes 102 can receive a surface electromyogram (SEMG or EMG) or like signal, such as can be acquired concurrently with or responsive to the electrostimulations being delivered by the stimulation electrodes in the grid 110. The responsive SEMG or other sensed signal from the sensing or recording electrodes 102 can be routed through isolation or buffer or bandpass or other filtering circuitry 104 and, in turn, to amplifier 106 circuitry or to other signal processing circuitry. The resulting SEMG or like response signal can be digitized and further signal-processed by digital-signal processing circuitry, such as can be included in the processor circuit 108. The signal-processed SEMG or like signal, or information derived therefrom, can be communicated to a local or remote user interface device 122, such as for further processing or display, such as via a wired or wireless communication unit 116. A battery 118 and power management circuitry 120 can also be provided within or coupled to the electrostimulation electronics unit 101.

The user interface device 122 can include a patient interface device, such as a mobile phone (e.g., smartphone), tablet computer, or other similar device. For example, the user interface device 122 can include a programmable application such as for communicating with the electrostimulation electronics unit 101, such as via the wireless communications unit 116. In an example, the user interface device 112 can include a graphical user interface or other similar configuration, such as for providing an electrostimulation response detector for receiving patient-subjective feedback from the particular patient about electrostimulations received by that particular patient. Such patient-subjective feedback can include information from the patient indicating how the electrostimulations are being sensed or experienced by the patient—e.g., can the electrostimulations be noticed, are they distracting, or are they uncomfortable? Such patient-subjective feedback can additionally or alternatively include information from the patient indicating how one or more symptoms (e.g., RLS or PLMD symptoms) to be alleviated in the patient (e.g., RLS or PLMD patient) are being experienced, either during an electrostimulation therapy session or after an electrostimulation session, such as at a particular electrostimulation energy level then being delivered to the patient. The user interface device 122 can include processor circuitry, such as can augment or supplant the processor or controller 108 onboard the electrostimulation electronics unit 101 of the system 100.

Additionally or alternatively to the patient-subjective feedback, such as can be received via the user interface device 122, objective information can be acquired from the patient such as together with delivery of electrostimulations of a particular electrostimulation energy parameter level to the patient during a therapy session. An example of such objective information can include providing an electrostimulation response detector that can detect and measure the SEMG signal response, such as can be obtained via the recording electrodes 102. Another example can include providing a response detector that can detect and measure patient (e.g., leg) movement information, such as can be obtained via a response detector that can include one or more other sensors 124 such as an accelerometer or inertial measurement unit (IMU), such as can be included onboard the electrostimulation electronics unit 101 or its wearable attachment thereto.

Figure 2:
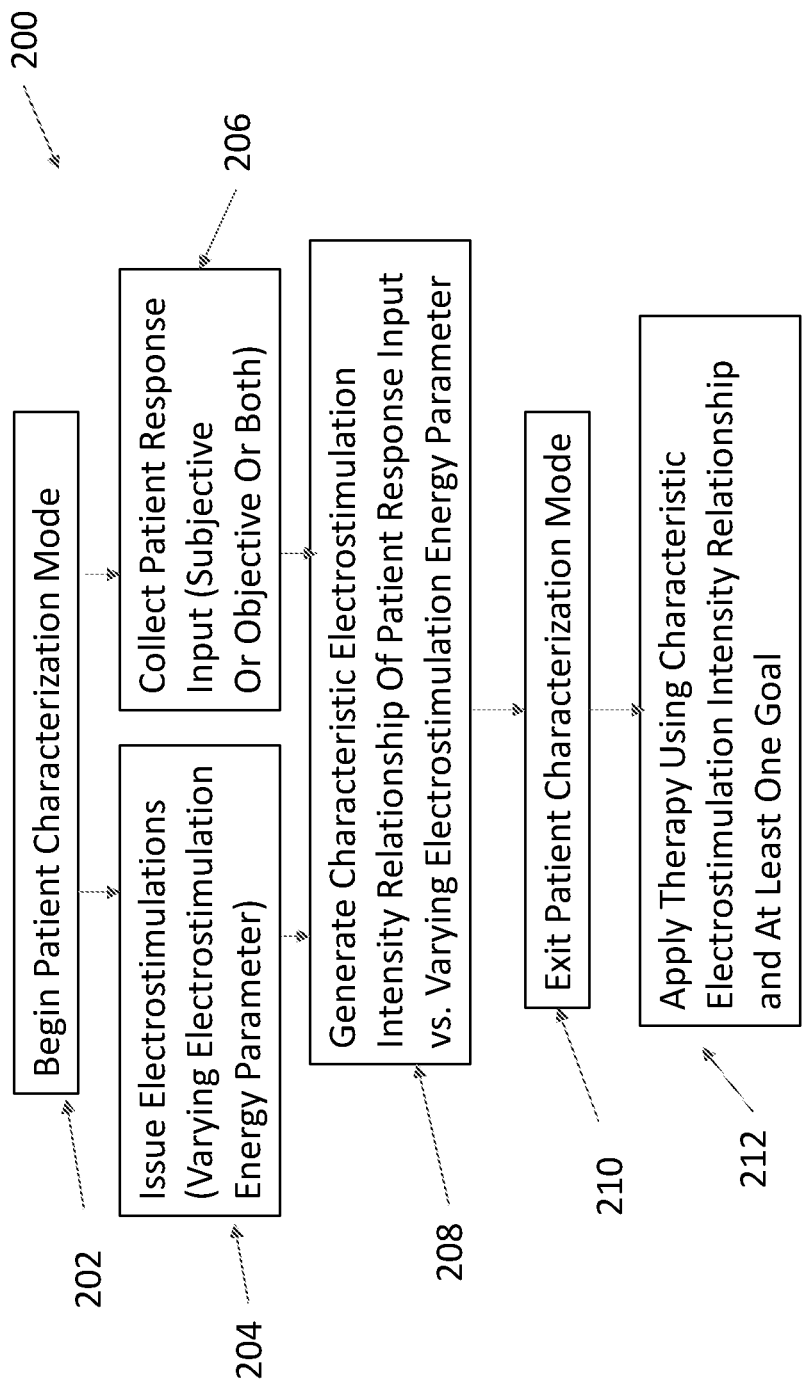
FIG. 2 shows an example of portions of a process, such as using the example of the system of FIG. 1, to determine a characteristic electrostimulation intensity relationship between a patient response input and a varying electrostimulation energy parameter.

FIG. 2 shows an example of portions of a process 200, such as using the example of the system 100 of FIG. 1, to determine a characteristic electrostimulation intensity relationship between a patient response input and a varying electrostimulation energy parameter.

At 202, a patient characterization mode of operating the electrostimulation electronics unit 101 can be initiated. For example, this can include putting the processor or controller 108 into a patient characterization mode, at 202.

At 204, in the patient characterization mode, the processor can control operation of the electrostimulation signal generator 114 to control issuing, at 204, neural electrostimulation pulses ("electrostimulations") with a slowly varying electrostimulation energy parameter (e.g., slowly varying electrostimulation current, electrostimulation voltage, electrostimulation pulsewidth duration, or a combination of these).

At 206, concurrent with issuing electrostimulations at 204, the processor can control the electrostimulation electronics unit 101 to collect, store, or process patient response input (e.g., subjective, objective, or both) to one or multiple electrostimulations issued for a particular value of the varying electrostimulation energy parameter or for a particular combination of electrostimulation energy parameters, one or more of which is being varied slowly enough to accommodate obtaining the patient response input.

At 208, after patient response input has been gathered over multiple values of the electrostimulation energy parameter or parameter combination, a "characteristic electrostimulation intensity relationship" can be generated between (or based on) the acquired patient response input vs. the varying electrostimulation energy parameter, such as explained further below.

At 210, after the characteristic electrostimulation intensity relationship has been generated, the patient characterization mode of operating the electrostimulation electronics unit 101 can be exited.

At 212, a therapy session can be initiated or continued, using the generated characteristic electrostimulation intensity relationship and at least one "goal" (as explained further below) to select a particular value of a variable operating point based upon the generated characteristic relationship, such as to operate the electrostimulation electronics unit 101 in accordance with the at least one goal. For example, the goal can include maintaining a consistent sensation level experienced by the patient, and the variable operating point can include selecting an electrostimulation current and pulsewidth along a strength-duration curve with the goal of maintaining such consistent sensation level for treating the RLS or PLMD patient, thereby providing therapy in a manner that is consistent with promoting relaxation and sleep.

Although FIG. 2 has been described as having separate modes for patient characterization and subsequent therapy application, the present techniques can include carrying out patient characterization during normal therapy delivery, rather than providing a separate mode for patient characterization, such as explained above with respect to FIG. 2.

Figure 3:
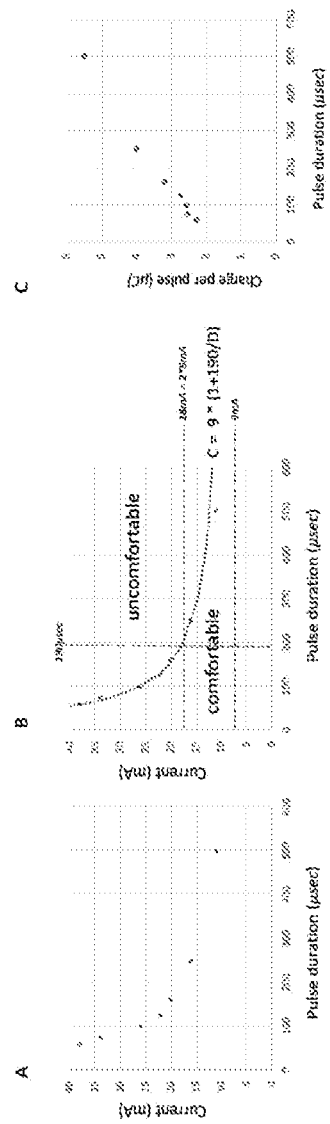
FIGS. 3A, 3B, and 3C show experimental data representing a particular illustrative example of generating a characteristic electrostimulation intensity relationship for a particular patient, such as by operating the electrostimulation electronics unit in a patient characterization mode.

FIGS. 3A, 3B, and 3C show experimental data representing a particular illustrative example of generating a characteristic electrostimulation intensity relationship (e.g., a strength-duration curve between at least one electrostimulation amplitude parameter (electrostimulation pulse current or voltage) and at least one electrostimulation timing parameter (e.g., electrostimulation pulsewidth, interpulse interval, frequency, or pulse shape) for a particular patient, such as by operating the electrostimulation electronics unit 101 in a patient characterization mode, as explained above. FIG. 3A shows an experimental graph of electrostimulation therapy signal pulse current amplitude (milliamperes) vs. electrostimulation therapy signal timing parameter, e.g., pulsewidth (microseconds). FIG. 3B shows a similar experimental graph, wherein the characteristic relationship has been constructed using patient-subjective feedback (e.g., input collected via the user-interface device 122) regarding whether the sensation being experienced by the patient during a period while electrostimulations are being delivered is "comfortable" or "uncomfortable". One or more electrostimulation energy amplitude parameters (e.g., electrostimulation pulse current, electrostimulation pulse voltage, or the like) and electrostimulation timing parameters (e.g., pulsewidth) can be varied during the patient characterization period while the patient-subjective input is being collected, such that data can be collected for generating the characteristic electrostimulation intensity relationship. FIG. 3C shows a graph of conceptual data of charge delivered (microCoulombs) vs. electrostimulation pulsewidth duration, as explained below.

FIGS. 3A, 3B, and 3C can be used to describe a specific example of using the present techniques for maintaining (1) consistent therapeutic relief and (2) consistent subjective perceptual sensations by a particular patient, while varying the neural electrostimulation waveform, such as can help inhibit or prevent biological adaptation or habituation, such as can be due to neural accommodation or neural plasticity.

The present techniques can assume that there is a therapeutic range of transcutaneous neural electrostimulation waveforms, for example, such as can include rectangular pulses that can be pulsed at a pulse-repetition frequency between 100 Hz and 10,000 Hz. The present techniques can also be applied to other pulses, for example, such as semi-rectangular pulses (e.g., trapezoidal pulses).

The present techniques can help identify or define a family of neural electrostimulation therapy signal waveforms within this therapeutic range, each of which induces similar perceptual sensations by the particular patient. This family of therapeutic neural electrostimulation waveforms can be governed or represented by a "characteristic electrostimulation intensity relationship," such as an equation or formula or a strength-duration relationship, such as which can indicate a particular desired neural electrostimulation, e.g., current amplitude given a particular neural electrostimulation pulsewidth (or vice versa).

For example, for a particular patient, the present techniques can generate a characteristic stimulation intensity relationship that can employ an equation that is similar to Lapicque's equation, which describes the response of an excitable neural structure to an electrical stimulus. More particularly, Lapicque's equation states that the current of a stimulation pulse (C) required to activate the neural structure is related to the pulse duration of that stimulation pulse (D) by the formula: $C=r*(1+(c/D))$, where "r" and "c" can represent constants. For example, for transcutaneous neurostimulation of the peroneal nerve, a similar formula applies, which is remarkable given the multiple layers of tissue (e.g., skin, fat, etc.) between the locus of the electrical stimulus and the stimulated nerve, such as which could potentially distort the electrical neurostimulation signal. The present techniques can leverage this type of equation or formula, such as to help enable consistency of perceptual sensations by the patient and consistency of therapeutic relief of RLS for the patient.

FIGS. 3A, 3B, and 3C illustrate an example of a process for defining a family of neural electrostimulation waveforms for a particular electrostimulation intensity threshold for a particular nerve target in a particular person or patient. In this experiment, represented in FIGS. 3A, 3B, and 3C, transcutaneous neural electrostimulation was applied to a particular patient at a location over the head of the fibula (near the most superficial aspect of the peroneal nerve) with multiple waveforms (FIG. 3A). Each point on FIG. 3A corresponds to the maximal comfortable current (discomfort threshold) for a given neural electrostimulation pulse duration (with comfort or discomfort being as indicated by patient-subjective input obtained from the patient), where comfort is limited by the intensity of perceptual sensations (FIG. 3A). The relationship between electrostimulation current (C, in milliamperes) and electrostimulation pulse duration (D, in microseconds) is fit well by the following inverse characteristic stimulation intensity relationship: $C=9*(1+190/D)$.

FIG. 3B shows this characteristic stimulation intensity relationship curve overlaid on the data from FIG. 3A. In FIG. 3B, points below the characteristic relationship curve are "comfortable" for the particular patient, points above the characteristic stimulation intensity relationship curve are "uncomfortable" for the particular patient. In FIG. 3B, the characteristic stimulation intensity relationship curve defines the maximal electrostimulation amplitude parameter (in this instance, current intensity) that is comfortable at each value of a corresponding electrostimulation timing parameter (e.g., pulse duration). Since there is a horizontal asymptote at +9 milliamperes, the neurostimulation charge delivered per electrostimulation pulse would be minimized at shorter pulse durations (see FIG. 3C). Thus, at a constant pulse repetition frequency, the average electrostimulation current would be minimized at shorter pulse durations.

To generalize somewhat, the above example can be used to describe a process to determine a "characteristic electrostimulation intensity relationship" equation for maximal comfortable electrostimulation amplitude parameter, e.g., current (e.g., a discomfort threshold) for the particular patient across a range of timing parameter values, e.g., pulsewidth. In an example, this can be regarded as the maximum electrostimulation current amplitude that is compatible with sleep by the particular RLS or PLMD patient. While the example described above with respect to FIGS. 3A, 3B, and 3C involved patient characterization testing and patient-subjective feedback input at 7 pulse durations, such curve-fitting to determine a "characteristic electrostimulation intensity relationship" for a particular patient can be done with as few as 2 or 3 carefully chosen pulse durations and corresponding patient-subjective feedback input. A similar process can be used with a particular patient providing patient-subjective feedback input to determine one or more patient-specific thresholds other than the discomfort threshold, such as:

Minimal noticeable electrostimulation current (sensation threshold), which can be useful when sub-sensory stimulation is desired or needed, such as for treating RLS or PLMD.

Maximal tolerable current (tolerability threshold), which can be useful for suppression of severe RLS or PLMD symptoms such as while a patient is awake.

Minimal current that elicits muscle activation (motor threshold), which can be useful in cases in which muscle activation is associated with therapeutic relief, such as with RLS.

In an example, for one or more such threshold (e.g., discomfort threshold, sensation threshold, tolerability threshold, motor threshold) patient-subjective feedback input can be obtained from the particular patient to which neural electrostimulations are being applied, such as via a response detector that can be included in the user interface device 122. Based at least in part on such patient-subjective feedback input, and available information to the controller 108 or the electrostimulation signal generator 114 about electrostimulation energy parameters of the electrostimulation being delivered to the patient, the characteristic relationship can be generated. As explained elsewhere herein, the motor threshold need not be obtained using patient-subjective feedback input; instead, such information can make use of SEMG response information such as can be measured from SEMG recording electrodes 102.

In an example, generating a characteristic electrostimulation intensity relationship can include inferring a characteristic electrostimulation intensity relationship formula from the electrostimulation energy parameters and the patient-subjective feedback. In an example, the system 100 can first use this information to infer the characteristic relationship formula associated with the particular threshold of interest (e.g., discomfort threshold, sensation threshold, tolerability threshold, motor threshold). For each of a small number of electrostimulation pulsewidths (e.g., 75 microseconds, 125 microseconds, 200 microseconds, or the like), the electrostimulation signal generator 114 can programmably increase the neural electrostimulation energy intensity (e.g., electrostimulation current amplitude) until the applicable threshold is reached, such as can be determined based on subjective feedback from the patient (or based upon sensed EMG activity in the case of motor threshold formula inference). Based on these data points (e.g., electrostimulation energy intensity and corresponding pulsewidth duration), the coefficients of the equation can be determined and a "personalized strength-duration curve" or similar characteristic electrostimulation intensity relationship can be calculated, such as by the controller 108 or using microprocessor circuitry included in the user interface device 122. Three points (and in some cases as few as two points) can be sufficient to infer an adequately predictive curve or even a piecewise linear representation of such a curve. During the process of generating a characteristic relationship, for each neural electrostimulation pulsewidth and corresponding electrostimulation current amplitude, the voltage required to generate the waveform can also be recorded, e.g., including at the applicable threshold of interest (e.g., discomfort threshold, sensation threshold, tolerability threshold, motor threshold), such as can be used to estimate power (see, e.g., applications explained further below).

Most points on the personalized strength-duration curve (or like characteristic relationship) are likely to have similar therapeutic efficacy. However, some cases there may be therapeutic range(s) on the curve and non-therapeutic range(s); in such cases, the portion of the curve used in the applications explained elsewhere herein can be defined as the therapeutic range(s) of the curve or like characteristic electrostimulation intensity relationship.

Figure 4:
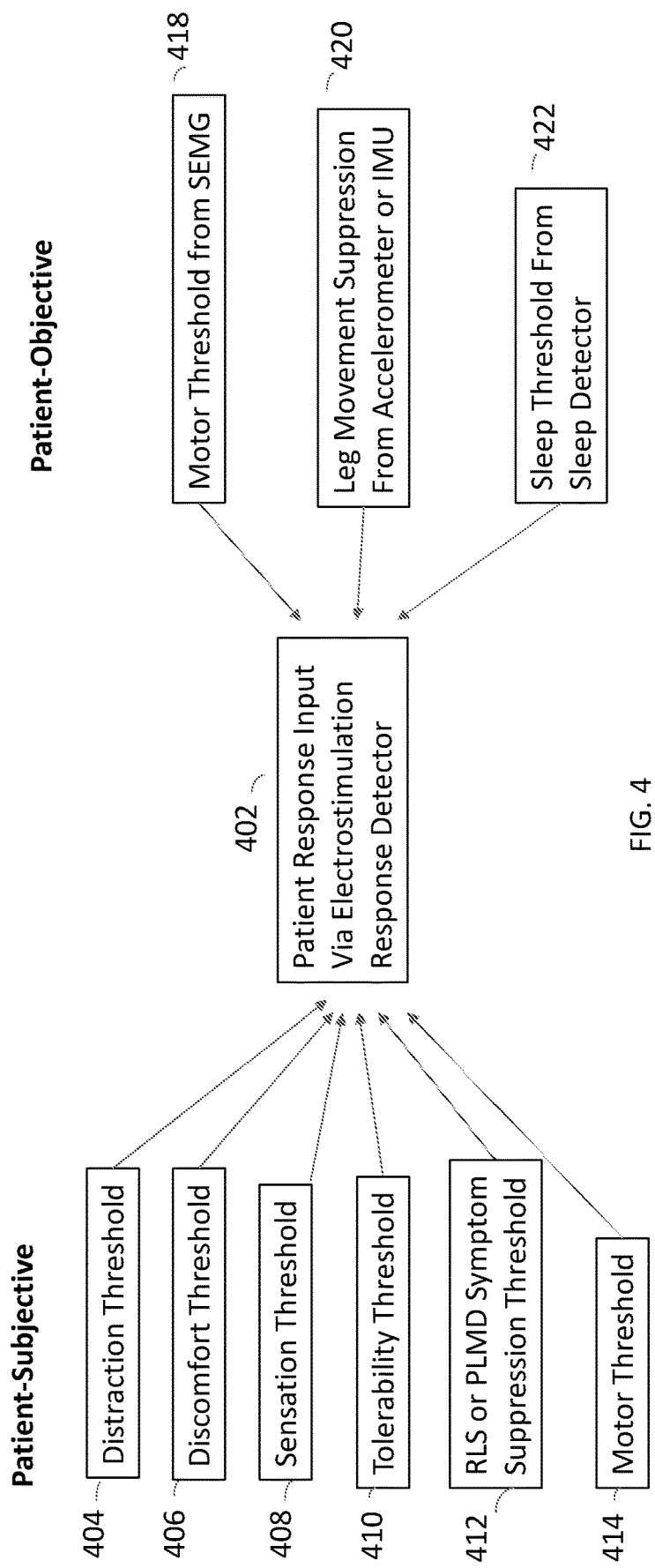
FIG. 4 shows an example of various types of patient response inputs that can be collected by an electrostimulation response detector that can be included in the system.

FIG. 4 shows an example of various types of patient response inputs that can be collected by an electrostimulation response detector that can be included in the system 100. For example, the user interface device 122 can include a graphical user interface or other patient feedback input device for collecting patient-subjective patient response input (e.g., distraction threshold 404, discomfort threshold 406, sensation threshold 408, tolerability threshold 410, RLS or PLMD symptom suppression threshold 412, or motor threshold 414, or any combination of these) from a particular patient (or patient caregiver). Additionally or alternatively, the electrostimulation electronics unit can include or be coupled to an electrostimulation response detector that can collect patient-objective input, such as can be measured by a sensor (e.g., motor threshold from SEMG 418, leg movement suppression from another sensor 124 such as an accelerometer or inertial measurement unit (IMU) 420, or sleep threshold from a sleep detector 422, or any combination of these).

As explained above, the patient-subjective patient response input can be collected while delivering electrostimulation pulses of varying electrostimulation energy parameters (e.g., electrostimulation current or voltage and electrostimulation pulsewidth duration), such as until the patient indicates that the applicable threshold has been met. As explained above, by increasing the electrostimulation energy parameter at a particular pulsewidth duration until the patient indicates that the applicable threshold has been met, then repeating the process at one or more other pulsewidth durations, a characteristic relationship can be determined, then used for subsequent delivery of electrostimulations in accordance with at least one goal.

At 404, the "distraction threshold" can be indicated by the patient-subjective input via a graphical user interface portion of an electrostimulation response detector in response to the varying electrostimulation energy parameter and a patient query via the graphical user interface. The "distraction threshold" can be a patient-subjective threshold level that is between the "sensation threshold" and "tolerability threshold." The distraction threshold can represent the highest level of electrostimulation energy that the patient reports as being compatible with sleep onset and maintenance, e.g., such that higher levels of electrostimulation energy are deemed by the patient to be too distracting to consistently allow for sleep. In an example, the distraction threshold is the default threshold used by the system 100. The distraction threshold can serve as an ideal upper limit upon electrostimulation energy level for bedtime or middle-of-the-night use to relieve one or more RLS symptoms at those times.

At 406, the "discomfort threshold" can be indicated by the patient-subjective input via a graphical user interface portion of an electrostimulation response detector in response to the varying electrostimulation energy parameter and a patient query via the graphical user interface. The "discomfort threshold" can be a patient-subjective threshold level that can represent the highest level of electrostimulation energy that the patient reports as being not uncomfortable, e.g., such that higher levels of electrostimulation energy are deemed by the patient to be too uncomfortable to be used with that particular patient. In an example, the discomfort threshold can be programmable to serve as a daytime default threshold used by the system 100.

At 408, the "sensation threshold" can be indicated by the patient-subjective input via a graphical user interface portion of an electrostimulation response detector in response to the varying electrostimulation energy parameter and a patient query via the graphical user interface. The "sensation threshold" can be a patient-subjective threshold level that can represent the highest level of electrostimulation energy that the patient reports as being not sensed by the patient, e.g., such that higher levels of electrostimulation energy are deemed by the patient to be noticeable sensations for that particular patient. In an example, the sensation threshold can be programmable to serve as threshold used by the system 100 for a patient who prefers sub-sensory electrostimulation for treating the RLS symptoms.

At 410, the "tolerability threshold" can be indicated by the patient-subjective input via a graphical user interface portion of an electrostimulation response detector in response to the varying electrostimulation energy parameter and a patient query via the graphical user interface. The "tolerability threshold" can be a patient-subjective threshold level that can represent the highest level of electrostimulation energy that the patient reports as being tolerable by the patient, e.g., such that higher levels of electrostimulation energy are deemed by the patient to be not tolerable by that particular patient, regardless of whether such higher levels of electrostimulation energy are actually uncomfortable for that particular patient. In an example, the tolerability threshold can be programmable to serve as threshold used by the system 100 for a patient who prefers using such a tolerability threshold for treating the RLS symptoms.

At 412, the "RLS or PLMD symptom suppression threshold" can be indicated by the patient-subjective input via a graphical user interface portion of an electrostimulation response detector in response to the varying electrostimulation energy parameter and a patient query via the graphical user interface. The "RLS or PLMD symptom suppression threshold" can be a patient-subjective threshold level that can represent an energy level deemed effective to suppress one or more RLS or PLMD symptoms." For example, the electrostimulation response detector can include a graphical user interface asking the particular patient to rate RLS symptoms (e.g., on a scale of 1 to 10, with 10 being most severe RLS symptoms) every N minutes (e.g., where N is in a specified range, such as between 0 and 60) while the patient has noticeable RLS symptoms and identifying the minimum electrostimulation current (or electrostimulation voltage) needed to suppress those RLS symptoms to below a certain specified absolute or relative level, such as based on the patient rating.

At 414, the "motor threshold" can be indicated by the patient-subjective input via a graphical user interface portion of an electrostimulation response detector in response to the varying electrostimulation energy parameter and a patient query via the graphical user interface. The "motor threshold" can be a patient-subjective threshold level indicative of one or more of the tonic muscle activation threshold, the phasic muscle activation threshold, the tonic motor threshold, or the like, such as reported by patient-subjective input provided by the patient or a caregiver.

At 418, the "motor threshold" can additionally or alternatively be indicated by the patient-objective input via a sensor input that can be detected and measured by the electrostimulation response detector in response to the varying electrostimulation energy parameter. For example, the "motor threshold" can be a patient-objective threshold level indicative of one or more of the tonic muscle activation threshold, the phasic muscle activation threshold, the tonic motor threshold, or the like, such as can be detected using the SEMG recording electrodes and associated front-end and signal processing circuitry.

At 420, the "leg movement suppression threshold" can additionally or alternatively be indicated by the patient-objective input via a sensor input that can be detected and measured by the electrostimulation response detector in response to the varying electrostimulation energy parameter. For example, the "leg movement suppression threshold" can be a patient-objective threshold level indicative of one or more of the tonic muscle activation threshold, the phasic muscle activation threshold, the tonic motor threshold, or the like, such as can be detected using leg movement indications provided by an accelerometer or inertial measurement unit (IMU) that can be included in the electrostimulation electronics unit 101. By measuring leg movements related to noticeable RLS symptoms and identifying the minimum electrostimulation current (or voltage) needed to suppress those leg movements below a certain level, a characteristic electrostimulation intensity relationship can be determined. Since RLS symptom severity is proportional to the frequency and magnitude of certain types of leg movements, this approach can be used to maintain the efficacy of the neural electrostimulation for treating the RLS symptom.

At 422, the "sleep threshold" can additionally or alternatively be indicated by the patient-objective input via a sleep sensor input that can be detected and measured by the electrostimulation response detector in response to the varying electrostimulation energy parameter. For example, the "sleep threshold" can be a patient-objective threshold level indicative of the minimum electrostimulation energy parameter level associated with a detected onset of a sleep of at least a specified first time period occurring within at least a specified second time period of initiation of the electrostimulations. Alternatively, the "sleep threshold" can be defined as a patient-objective threshold level indicative of the maximum level of electrostimulation energy that doesn't interfere with sleep or with a particular sleep state. The electrostimulation energy can be varied during the same therapy session, or over multiple therapy sessions, such as to detect an average time to sleep onset. The sleep detector can include one or more sleep sensors, such as can be based on one or more of: (1) an accelerometer or IMU sensor, such as onboard the electrostimulation electronics unit 101, providing indication of an amount of patient movement (e.g., leg movement) or patient posture or position associated with sleep; (2) polysomnogram (PSG) sleep detector, e.g., that can include using one or more of electroencephalogram, electro-oculogram, electromyogram, electrocardiogram, pulse oximetry, respiratory airflow or effort, or other sensed information to detect an onset of sleep or a particular sleep state; (3) an electroencephalogram (EEG) sleep detector, such as can detect sleep from EEG signal pattern; (4) a photoplethysmogram (PPG) sleep detector; (5) an electrocardiogram (ECG) sleep detector, such as can use heart rate variability (HRV) or other ECG characteristic to detect an onset of sleep or a particular sleep state; or the like.

A combination of multiple patient-subjective patient response inputs to the electrostimulations being delivered, patient objective patient response inputs to the electrostimulations being delivered, or both, can be combined, such as using a specified weighting of the different patient response inputs being combined. The resulting combination can form a composite patient response input that can be used, such as together with the at least one goal, to deliver subsequent electrostimulations to the particular patient from whom the patient response input(s) were obtained.

After (1) gathering the patient-subjective or patient-objective response input via the electrostimulation response detector, whether in a patient characterization mode or otherwise, and (2) generating the characteristic relationship, then the controller 108 can operate the electrostimulation signal generator 114 to issue subsequent electrostimulations using a variable operating point, such as along a curve representing the characteristic relationship, such as to help more efficiently and effectively provide therapy in accordance with at least one goal.

Figure 5:
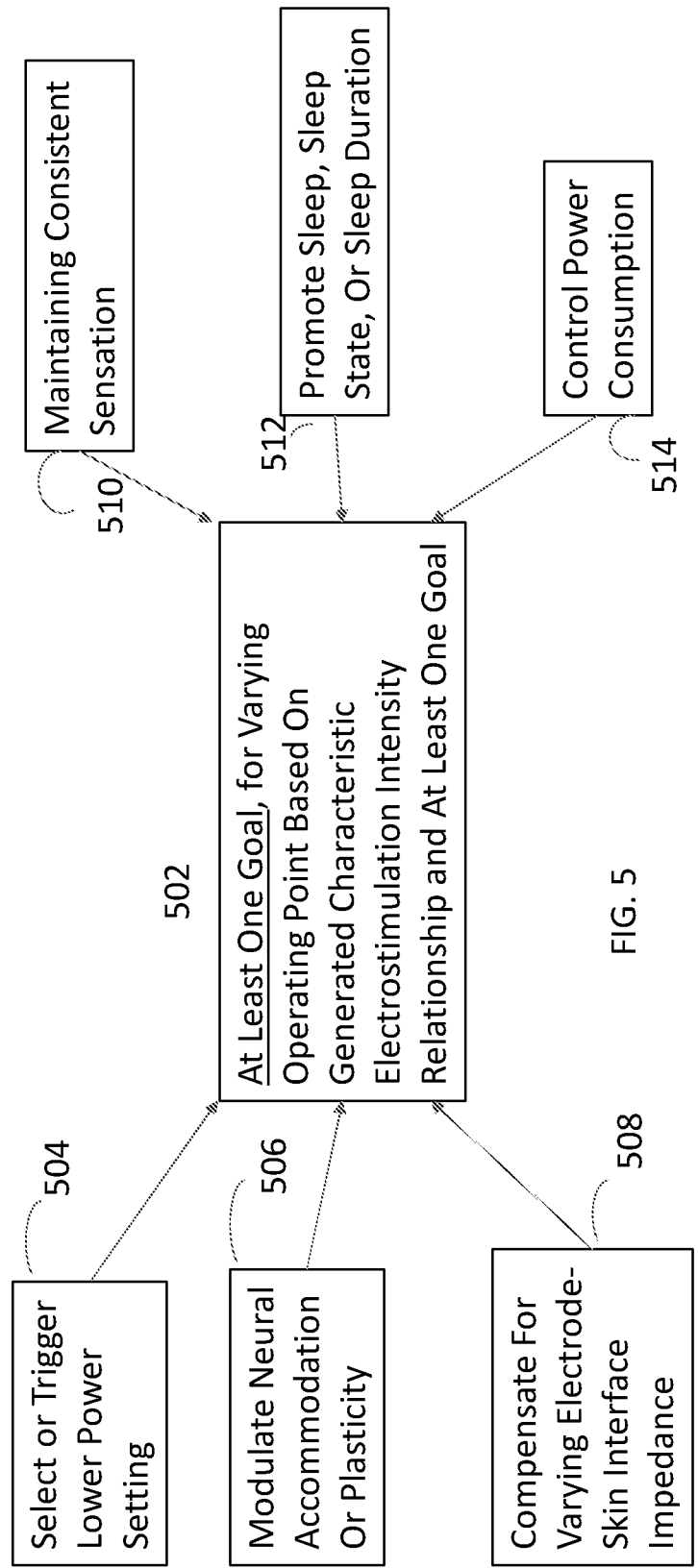
FIG. 5 shows examples of one or more goals that can be used as the at least one goal for varying the operating point based on the generated characteristic electrostimulation intensity relationship and the at least one goal.

FIG. 5 shows examples of one or more goals that can be used as the at least one goal, at 502, for varying the operating point based on the generated characteristic relationship and the at least one goal.

At 504, the at least one goal can include selecting or triggering a lower power setting. For example, this can include at least one of selecting or varying the operating point to select a lower power setting based on the generated characteristic relationship, such as can be triggered in response to an occurrence of at least one of: (i) a low battery condition, (ii) too high temperature or insufficient heat dissipation condition, or (iii) a long-duration neural electrostimulation session. Such selection or triggering can occur either at the beginning of a therapy session, or even during a therapy session.

For example, the decision by the controller 108 to shift from a higher power electrostimulation setting to a lower power electrostimulation setting can be based on one or more of: (1) a duration of the therapy session (e.g., total session duration, session duration to present, duration from present to end of session), (2) battery 118 life remaining, e.g., before recharging or replacement is needed, (3) estimated electrostimulation power consumption such as based on one or more of session duration, load impedance, or stimulation intensity of the therapy session (which can be based in part on past history of use).

In an example, the system 100 can first identify a characteristic relationship based on a patient-specific threshold (e.g., distraction threshold), irrespective of efficacy, in which the different points on a curve or other characteristic relationship vary in terms of power. The controller 108 can control the system 100 such as to cycle between higher power points on the characteristic relationship (which provide higher efficacy for symptom relief) and lower power points (which may have unknown, lower, or no efficacy for symptom relief). An advantage of such cycling is that, in such a configuration of operating, the system 100 can allow for a long-duration therapy session with a consistent sensory experience throughout the therapy session. This would avoid potentially distracting transitions between turning electrostimulation therapy "on" and "off". For example, this would allow a "3-hour session" that includes blocks of 30-min high-power electrostimulation interleaved by blocks of 60-min low-power electrostimulation.

In another example, the controller 108 can control operation of the system 100 to first identify a characteristic relationship based on a patient-specific threshold, irrespective of efficacy, where the points on the characteristic relationship vary in terms of power. The system 100 would cycle between higher power points (which could induce efficacious symptom relief) and lower power points (which could sustain but not reliably induce efficacious symptom relief). An advantage is that this system can provide a consistent sensory experience, while also reducing power consumption. For example, this would allow a "3-hour session" that includes a block of 30-min high-power followed by a block of 150-min low-power.

At 506, the at least one goal can include modulating at least one of neural accommodation or plasticity, including by varying the operating point based on the generated characteristic relationship. For example, such habituation effects can be reduced by varying the operating point on a patient-specific threshold characteristic relationship curve (e.g., discomfort threshold, sensation threshold, tolerability threshold, motor threshold, or some composite characteristic relationship of two or more of these). Such varying can be carried out by the controller 108 or electrostimulation signal generator 114 algorithmically or otherwise, such as randomly or pseudo-randomly.

At 508, the at least one goal can include compensating for varying electrode-skin interface impedance. This can include at least one of selecting or varying the operating point based on the generated characteristic relationship. For example, if load impedance (which includes electrode-tissue interface impedance) was very high, the system 100 may not have enough voltage or power to generate the desired electrostimulation current. In this case, the controller 108 or electrostimulation signal generator 114 can shift to a lower-power electrostimulation waveform on the same patient-specific threshold relationship characteristic curve.

At 510, the at least one goal can include maintaining consistent sensation for the particular patient. This can include varying the operating point based on the generated characteristic relationship. For example, at least some anecdotal data may indicate that patient sensation of the electrostimulation decreases over the course of a 30-minute electrostimulation therapy session. To maintain constant or consistent sensation and electrostimulation therapy efficacy, the controller 108 or electrostimulation signal generator 114 can vary the operating point along a consistent-efficacy relationship characteristic curve to an operating point on the consistent-efficacy relationship characteristic curve with higher sensations, particularly if doing so can save power without compromising therapy efficacy.

At 512, the at least one goal can include at least one of selecting or varying the operating point based on the generated characteristic relationship and at least one of a sleep state or sleep duration of the patient. For example, this approach can use historical data indicating efficacy based on sleep detection or sleep state detection (e.g., time-to-sleep, sleep duration, or the like) to select an operating point on a characteristic relationship curve indicating at least one of efficacy or efficiency.

To recap and further explain, once the system 100 has used the above-explained techniques to infer or generate a patient-specific relationship characteristic, which can be expressed by a curve or a formula, the controller 108 or electrostimulation signal generator 114 can deploy this inferred or generated patient-specific relationship characteristic curve or formula, such as for varying an operating point along the patient-specific relationship characteristic to meet one or more applications or goals.

For example, a goal can include enhancing therapeutic efficacy, such as by varying the electrostimulation waveform, such as to help reduce the rate and extent of neural accommodation and plasticity. In this technique, the system 100 can be controlled in a manner so as to shift the neural electrostimulation waveform between multiple operating points on the inferred or generated patient-specific characteristic relationship formula or curve for the patient, thus varying the neural stimulus while maintaining consistent perceptual sensations by the particular patient.

In an example, another goal can include reducing power, such as by shifting to or using lower-power electrostimulation waveforms on the same patient-specific characteristic relationship or curve. For example, this can be used in one or more of the following ways.

a. The default electrostimulation waveform can be changed to the lowest power electrostimulation waveform on the characteristic relationship or curve. This may not be a desired approach in validation situations in which it is not desired that each patient is to receive a different personalized waveform.

b. A lower power electrostimulation waveform on the characteristic relationship curve can be shifted to, but triggered only in cases or under conditions in which lower-power is operationally significant. Such cases can include one or more of: (i) low battery, (ii) too high temperature/insufficient heat dissipation, or (iii) long-duration stimulation session.

c. Allow shifting back-and-forth between lower-power and higher-power electrostimulation waveforms. This can be useful in cases of neural electrostimulation for long therapy session duration (e.g., hours) throughout a period of sleep for the particular patient. In such cases, it may be helpful to maintain consistency in perceptual sensations, such to help avoid waking the patient. However, it may not be necessary to have effective (or equally-effective) therapy 100% of the time during such a long duration electrostimulation therapy session. This technique can be used to help enable or permit alternating between highly-effective therapy and less-effective therapy without waking the patient. Therefore, in this case, selecting low-power waveforms outside the therapeutic range can be an option.

In any of these cases, the present systems, methods, and techniques can be used to estimate the average power ($P_{rms}$) needed such as for individual ones of the multiple waveforms on the characteristic relationship curve, such as can be determined before implementing this approach. $P_{rms}=I_{rms}*V$, where the $I_{rms}$ (average electrostimulation current) can be calculated directly from the specified electrostimulation being delivered according to the characteristic relationship curve, but in which voltage, V, determination can involve estimation. Voltage, V, can be estimated such as by interpolating the voltage data from the characteristic relationship formula inference or generation process.

In an example, a goal can include compensating for higher impedance by shifting to lower-impedance waveforms on the same curve. This can be used in situations with relatively high electrode-skin interface impedance. Such high impedance can occur when hydrogel electrodes are re-used for numerous electrostimulation therapy sessions. Therefore, this approach could be used to extend the lifespan of electrode usage. This can be used in the following ways:

a. Change the default electrostimulation waveform to the lowest impedance electrostimulation waveform on the characteristic relationship curve. While appealing, this may imply that each patient would receive a different personalized waveform, which may not be desirable in certain validation scenarios.

b. Shift to a lower impedance waveform on the characteristic relationship curve in cases or under conditions in which the system 100 cannot generate the voltage needed to deliver the programmed electrostimulation current. Because shorter electrostimulation pulse durations can be associated with lower impedance, the system 100 can minimize impedance by shifting to the shortest pulse duration within the therapeutic range of the curve. Optionally, a maximum electrostimulation current limit can be increased or even disabled when operating using the shortest electrostimulation pulse duration, if desired.

While much of the above description has focused on implementation using a constant electrostimulation current mode for delivering the electrostimulations, the present techniques can similarly be applied in a constant electrostimulation voltage mode for delivering the electrostimulations. Also, much of the above description has focused on application of the present techniques in a particular RLS or PLMD patient to relieve particular RLS or PLMD systems, such as to promote sleep. Such neural electrostimulation considerations for RLS or PLMD can be very different than other neural electrostimulation applications for other physiological conditions or symptoms. Nonetheless, the present techniques may find applicability in treating other types of patients with other types of symptoms, in certain circumstances. For example, the present techniques can be used in treating a patient having focal dystonia, such as explained in the above-incorporated (8) Raghunathan et al. U.S. Provisional Patent Application Ser. No. 63/015,758, SYSTEMS AND METHODS FOR TREATMENT OF FOCAL DYSTONIA OR OVERACTIVE NERVES, filed on Apr. 27, 2020. Similar to the description included herein, patient-subjective input from an electrostimulation response detector that can include a patient user interface or patient-objective input from an electrostimulation response detector that can include sensing electrodes or other sensor, for example, can be used to develop a characteristic electrostimulation intensity relationship for delivering electrostimulation signals for treating the focal dystonia condition, as another illustrative example.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as The claimed invention is:

1. A system for treating a particular patient, having one or more symptoms associated with at least one of Restless Legs Syndrome (RLS) or Periodic Limb Movement Disorder (PLMD), using external transcutaneous neural electrostimulation therapy signals applied via at least one electrostimulation electrode configured for location at a first external target body location, the system comprising:
   an external, non-implantable electrostimulation unit, including:
   an electrostimulation signal generator, coupled to the at least one electrostimulation electrode to generate and deliver a plurality of electrostimulation therapy signals to the particular patient to treat at least one RLS or PLMD symptom, wherein an individual electrostimulation therapy signal comprises a pulsed electrical signal having a stimulation intensity characterized by at least one amplitude parameter and at least one timing parameter;
   an electrostimulation response detector to receive at least one of RLS or PLMD electrostimulation response indications of the particular patient to the individual ones of the plurality of electrostimulation therapy signals;
   a controller coupled to the electrostimulation signal generator and the electrostimulation response detector, to control individual ones of the plurality of electrostimulation therapy signals generated and delivered by the electrostimulation signal generator and to receive the at least one of RLS or PLMD electrostimulation response indications to individual ones of the plurality of electrostimulation therapy signals from the electrostimulation response detector, wherein the controller:
   determines a respective at least one of an RLS or PLMD response indication threshold amplitude parameter for the particular patient at a plurality of values of one of the at least one timing parameter;
   generates a characteristic electrostimulation intensity relationship based on the determined respective at least one of an RLS or PLMD response indication threshold amplitude parameter and the plurality of values of one of the at least one timing parameter; and
   generates and applies subsequent electrostimulation therapy signals to the particular patient according to (1) at least one goal and (2) a variable operating point based upon the generated characteristic electrostimulation intensity relationship.

2. The system of claim 1, in which the controller generates the characteristic electrostimulation intensity relationship determined using patient feedback input from the particular patient via the electrostimulation response detector providing the at least one of RLS or PLMD response indication threshold amplitude parameter including at least one or a combination or composite of:
   a patient-subjective distraction threshold amplitude parameter;
   a patient-subjective discomfort threshold amplitude parameter;
   a patient-subjective sensation threshold amplitude parameter; or
   a patient-subjective tolerability threshold energy parameter;
   a patient-subjective RLS or PLMD symptom suppression threshold energy parameter;
   a motor threshold energy parameter determined using input from sensing electrodes, externally associated with the particular patient, via the electrostimulation response detector;
   a leg movement suppression threshold energy parameter determined using input from an accelerometer or an inertial measurement unit (IMU), externally associated with the particular patient, via the electrostimulation response detector; or
   a sleep threshold energy parameter determined using input from a sleep detector sensor, externally associated with the particular patient, via the electrostimulation response detector.

3. The system of claim 2, in which the controller generates the characteristic electrostimulation intensity relationship based on the response indication threshold amplitude parameter including the patient-subjective distraction threshold amplitude parameter determined using patient feedback input from the particular patient via the electrostimulation response detector.

4. The system of claim 2, in which the controller generates the characteristic electrostimulation intensity relationship based on the response indication threshold amplitude parameter including the patient-subjective discomfort threshold amplitude parameter determined using patient feedback input from the particular patient via the electrostimulation response detector.

5. The system of claim 2, in which the controller generates the characteristic electrostimulation intensity relationship based on the response indication threshold amplitude parameter including a patient-subjective sensation threshold neural stimulation energy parameter determined using patient feedback input from the particular patient via the electrostimulation response detector.

6. The system of claim 2, in which the controller generates the characteristic electrostimulation intensity relationship based on the response indication threshold amplitude parameter including a patient-subjective tolerability threshold energy parameter determined using patient feedback input from the particular patient via the electrostimulation response detector.

7. The system of claim 2, in which the controller generates the characteristic electrostimulation intensity relationship based on the response indication threshold amplitude parameter including a patient-subjective RLS or PLMD symptom suppression threshold energy parameter determined using patient feedback input from the particular patient via the electrostimulation response detector.

8. The system of claim 2, in which the controller generates the characteristic electrostimulation intensity relationship based on the response characteristic threshold amplitude parameter including a motor threshold energy parameter determined using input from sensing electrodes, externally associated with the particular patient, via the electrostimulation response detector.

9. The system of claim 2, in which the controller generates the characteristic electrostimulation intensity relationship based on the response characteristic threshold amplitude parameter including a leg movement suppression threshold energy parameter determined using input from an accelerometer or an inertial measurement unit (IMU), externally associated with the particular patient, via the electrostimulation response detector.

10. The system of claim 2, in which the controller generates the characteristic electrostimulation intensity relationship based on the response characteristic threshold amplitude parameter including a sleep threshold energy parameter determined using input from a sleep detector sensor, externally associated with the particular patient, via the electrostimulation response detector.

11. The system of claim 1, in which the controller determines the variable operating point based upon the generated characteristic electrostimulation intensity relationship and the at least one goal includes at least one or a combination or composite of:
  selecting a lower power setting, including by at least one of selecting or varying the operating point based on the generated characteristic electrostimulation intensity relationship, in response to an occurrence of at least one of: (i) a low battery condition, (ii) too high temperature or insufficient heat dissipation condition, or (iii) a long-duration neural electrostimulation session;
  modulating at least one of neural accommodation or plasticity, including by varying the operating point based on the generated characteristic electrostimulation intensity relationship;
  compensating for varying electrode-skin interface impedance, including by at least one of selecting or varying the operating point based on the generated characteristic electrostimulation intensity relationship;
  maintaining consistent sensation for the particular patient, including by varying the operating point based on the generated characteristic electrostimulation intensity relationship;
  at least one of selecting or varying the operating point based on the generated characteristic electrostimulation intensity relationship and at least one of a sleep state or sleep duration of the patient; or
  controlling power consumption, including by at least one of selecting or varying the operating point based on the generated characteristic electrostimulation intensity relationship.

12. The system of claim 11, in which the controller determines the variable operating point based upon the generated characteristic electrostimulation intensity relationship and the at least one goal includes selecting a lower power setting, including by at least one of selecting or varying the operating point based on the generated characteristic electrostimulation intensity relationship, in response to an occurrence of at least one of: (i) a low battery condition, (ii) too high temperature or insufficient heat dissipation condition, or (iii) a long-duration neural electrostimulation session.

13. The system of claim 11, in which the processor circuitry determines the variable operating point based upon the generated characteristic electrostimulation intensity relationship and the at least one goal includes modulating at least one of neural accommodation or plasticity, including by varying the operating point based on the generated characteristic electrostimulation intensity relationship.

14. The system of claim 11, in which the controller determines the variable operating point based upon the generated characteristic electrostimulation intensity relationship and the at least one goal includes compensating for varying electrode-skin interface impedance, including by at least one of selecting or varying the operating point based on the generated characteristic electrostimulation intensity relationship.

15. The system of claim 11, in which the controller determines the variable operating point based upon the generated characteristic electrostimulation intensity relationship and the at least one goal includes maintaining consistent sensation for the particular patient, including by varying the operating point based on the generated characteristic electrostimulation intensity relationship.

16. The system of claim 11, in which the controller determines the variable operating point based upon the generated characteristic electrostimulation intensity relationship and the at least one goal includes at least one of selecting or varying the operating point based on the generated characteristic electrostimulation intensity relationship and at least one of a sleep state or sleep duration of the patient.

17. The system of claim 11, in which the controller determines the variable operating point based upon the generated characteristic electrostimulation intensity relationship and the at least one goal includes controlling power consumption, including by at least one of selecting or varying the operating point based on the generated characteristic electrostimulation intensity relationship.

18. The system of claim 1, in which the controller is coupled to the electrostimulation signal generator to control issuing electrostimulations to vary the operating point, including by varying neural electrostimulation pulsewidth duration and at least one of current or voltage.

19. The system of claim 18, in which the controller is coupled to the electrostimulation signal generator to control issuing electrostimulations to vary the operating point, including by varying neural electrostimulation pulsewidth duration and at least one of current or voltage over a constrained specified deemed efficacious range of pulsewidth durations.

20. The system of claim 1, in which the controller is coupled to the electrostimulation signal generator to control issuing electrostimulations to shift between relatively higher power waveform electrostimulations and relatively lower power waveform electrostimulations.

21. The system of claim 20, in which the controller controls issuing electrostimulations to shift between relatively higher power waveform electrostimulations and relatively lower power waveform electrostimulations based on at least one of: (1) a therapy session duration; (2) battery life remaining; or (3) estimated power consumption.

22. The system of claim 1, in which the controller is coupled to the electrostimulation signal generator to control issuing electrostimulations to vary the operating point based on the generated characteristic electrostimulation intensity relationship and in at least partially random or pseudo-random manner.

23. The system of claim 1, in which the electrostimulation response detector further includes at least one of:
  electrostimulation voltage response detector circuitry to measure the electrostimulation voltage response to an electrostimulation therapy signal having a specified electrostimulation current, and wherein the processor determines at least one of a power or an electrode interface impedance based at least in part on the measured electrostimulation voltage response; and
  electrostimulation current response detector circuitry to measure the electrostimulation current response to an electrostimulation therapy signal having a specified electrostimulation voltage, and wherein the processor determines at least one of a power or an electrode interface impedance based at least in part on the measured electrostimulation current response.

24. A system for treating a particular patient using external transcutaneous neural electrostimulation therapy signals applied via at least one electrostimulation electrode configured for location at a first external target body location, the system comprising:
   an external, non-implantable electrostimulation unit, including:
   an electrostimulation signal generator, coupled to the at least one electrostimulation electrode to deliver a plurality of electrostimulation therapy signals to the particular patient, wherein an individual electrostimulation therapy signal comprises a pulsed electrical signal having a stimulation intensity characterized by at least one amplitude parameter and at least one timing parameter;
   an electrostimulation response detector to receive electrostimulation response indications of the particular patient to the corresponding electrostimulation therapy signals;
   a controller, coupled to the electrostimulation signal generator and the electrostimulation response detector, to control the generation and delivery of individual electrostimulation therapy signals and to receive the electrostimulation response indications from the electrostimulation response detector, wherein the controller:
   determines a respective response indication threshold amplitude parameter for the particular patient at a plurality of values of one of the at least one timing parameters;
   generates a characteristic electrostimulation intensity relationship based on the determined respective response indication threshold amplitude parameters and the plurality of values of the at least one timing parameter; and
   generates and applies subsequent electrostimulation therapy signals to the particular patient according to (1) at least one goal and (2) a variable operating point based upon the generated characteristic electrostimulation intensity relationship; and
   wherein the controller determines the variable operating point based upon the generated characteristic electrostimulation intensity relationship and the at least one goal includes at least one or a combination or composite of:
   selecting a lower power setting, including by at least one of selecting or varying the operating point based on the generated characteristic electrostimulation intensity relationship, in response to an occurrence of at least one of: (i) a low battery condition, (ii) too high temperature or insufficient heat dissipation condition, or (iii) a long-duration neural electrostimulation therapy signal delivery;
   modulating at least one of neural accommodation or plasticity, including by varying the operating point based on the generated characteristic electrostimulation intensity relationship;
   compensating for varying electrode-skin interface impedance, including by at least one of selecting or varying the operating point based on the generated characteristic electrostimulation intensity relationship;
   maintaining consistent sensation for the particular patient, including by varying the operating point based on the generated characteristic electrostimulation intensity relationship;
   at least one of selecting or varying the operating point based on the generated characteristic electrostimulation intensity relationship and at least one of a sleep state or sleep duration of the patient; or
   controlling power consumption, including by at least one of selecting or varying the operating point based on the generated characteristic electrostimulation intensity relationship.

25. A system for treating a particular patient using external transcutaneous neural electrostimulation therapy signals applied via at least one electrostimulation electrode configured for location at a first external target body location, the system comprising:
   an external, non-implantable electrostimulation unit, including:
   an electrostimulation signal generator, coupled to the at least one electrostimulation electrode to deliver a plurality of electrostimulation therapy signals to the particular patient, wherein an individual electrostimulation therapy signal comprises a pulsed electrical signal having a stimulation intensity characterized by at least one amplitude parameter and at least one timing parameter;
   an electrostimulation response detector to receive electrostimulation response indications of the particular patient to the corresponding electrostimulations;
   a controller, coupled to the electrostimulation signal generator and the electrostimulation response detector, to control the generation and delivery of individual electrostimulation therapy signals and to receive the electrostimulation response indications from the electrostimulation response detector, wherein the controller:
   determines a respective response indication threshold amplitude parameter for the particular patient at a plurality of values of one of the at least one timing parameter;
   generates a characteristic electrostimulation intensity relationship based on the determined respective response indication threshold amplitude parameters and the plurality of values of one of the at least one timing parameter; and
   generates and applies subsequent electrostimulation therapy signals to the particular patient according to (1) at least one goal and (2) a variable operating point based upon the generated characteristic electrostimulation intensity relationship; and
   wherein the controller generates the characteristic electrostimulation intensity relationship determined using patient feedback input from the particular patient via the electrostimulation response detector providing the response indication threshold amplitude parameter including at least one or a combination or composite of:
   a patient-subjective distraction threshold amplitude parameter;
   a patient-subjective discomfort threshold amplitude parameter;
   a patient-subjective sensation threshold amplitude parameter; or
   a patient-subjective tolerability threshold amplitude parameter;
   a patient-subjective symptom suppression threshold amplitude parameter;
   a motor threshold amplitude parameter determined using input from sensing electrodes, externally associated with the particular patient, via the electrostimulation response detector;

a leg movement suppression threshold amplitude parameter determined using input from an accelerometer or an inertial measurement unit (IMU), externally associated with the particular patient, via the electrostimulation response generator; or a sleep threshold amplitude parameter determined using input from a sleep detector sensor, externally associated with the particular patient, via the electrostimulation response detector.

26. A method for treating a particular patient, having one or more symptoms associated with at least one of Restless Legs Syndrome (RLS) or Periodic Limb Movement Disorder (PLMD), using external transcutaneous neural electrostimulation therapy signals applied via at least one electrostimulation electrode configured for location at a first external target body location, the method comprising:

generating and delivering a plurality of transcutaneous electrostimulation therapy signals to the particular patient to treat at least one RLS or PLMD symptom, wherein an individual electrostimulation therapy signal comprises a pulsed electrical signal having a stimulation intensity characterized by at least one amplitude parameter and at least one timing parameter;

receiving at least one of RLS or PLMD electrostimulation response indications of the particular patient to the individual ones of the plurality of electrostimulation therapy signals;

controlling individual ones of the plurality of electrostimulation therapy signals generated and delivered and receiving the corresponding electrostimulation response indications to individual ones of the plurality of electrostimulation therapy signals;

determining a respective at least one of an RLS or PLMD response indication threshold amplitude parameter for the particular patient at a plurality of values of one of the at least one timing parameter;

generating a characteristic electrostimulation intensity relationship based on the determined respective at least one of an RLS or PLMD response indication threshold amplitude parameter and the plurality of values of one of the at least one timing parameter; and generating and applying subsequent electrostimulation therapy signals to the particular patient according to (1) at least one goal and (2) a variable operating point based upon the generated characteristic electrostimulation intensity relationship.

27. The method of claim 26, wherein the characteristic electrostimulation intensity relationship is determined using patient feedback input from the particular patient providing the response indication threshold amplitude parameter including at least one or a combination or composite of:

a patient-subjective distraction threshold amplitude parameter;

a patient-subjective discomfort threshold amplitude parameter;

a patient-subjective sensation threshold amplitude parameter; or a patient-subjective tolerability threshold amplitude parameter;

a patient-subjective symptom suppression threshold amplitude parameter;

a motor threshold amplitude parameter determined using input from sensing electrodes, externally associated with the particular patient, via the electrostimulation response detector;

a leg movement suppression threshold amplitude parameter; or a sleep threshold amplitude parameter.

28. A method for treating a particular patient, having one or more symptoms associated with at least one neural condition, using external transcutaneous neural electrostimulation therapy signals applied via at least one electrostimulation electrode configured for location at a first external target body location, the method comprising:

generating and delivering a plurality of transcutaneous electrostimulation therapy signals to the particular patient to treat at least one symptom, wherein an individual electrostimulation therapy signal comprises a pulsed electrical signal having a stimulation intensity characterized by at least one amplitude parameter and at least one timing parameter;

receiving electrostimulation response indications of the particular patient to the individual ones of the plurality of electrostimulation therapy signals;

controlling individual ones of the plurality of electrostimulation therapy signals generated and delivered and receiving the corresponding electrostimulation response indications to individual ones of the plurality of electrostimulation therapy signals;

determining a respective a response indication threshold amplitude parameter for the particular patient at a plurality of values of one of the at least one timing parameter;

generating a characteristic electrostimulation intensity relationship based on the determined respective response indication threshold amplitude parameter and the plurality of values of one of the at least one timing parameter; and generating and applying subsequent electrostimulation therapy signals to the particular patient according to (1) at least one goal and (2) a variable operating point based upon the generated characteristic electrostimulation intensity relationship; and wherein determining the variable operating point based upon the generated characteristic electrostimulation intensity relationship and the at least one goal includes at least one or a combination or composite of:

selecting a lower power setting, including by at least one of selecting or varying the operating point based on the generated characteristic electrostimulation intensity relationship, in response to an occurrence of at least one of: (i) a low battery condition, (ii) too high temperature or insufficient heat dissipation condition, or (iii) a long-duration neural electrostimulation therapy signal delivery;

modulating at least one of neural accommodation or plasticity, including by varying the operating point based on the generated characteristic electrostimulation intensity relationship;

compensating for varying electrode-skin interface impedance, including by at least one of selecting or varying the operating point based on the generated characteristic electrostimulation intensity relationship;

maintaining consistent sensation for the particular patient, including by varying the operating point based on the generated characteristic electrostimulation intensity relationship;

at least one of selecting or varying the operating point based on the generated characteristic electrostimulation intensity relationship and at least one of a sleep state or sleep duration of the patient; or controlling power consumption, including by at least one of selecting or varying the operating point based on the generated characteristic electrostimulation intensity relationship.

29. The method of claim 28, wherein the at least one neural condition includes at least one of RLS or PLMD, and wherein the generated characteristic electrostimulation intensity relationship corresponds to at least one symptom of the at least one of RLS or PLMD.

30. The method of claim 28, wherein the at least one neural condition includes focal dystonia, and wherein the generated characteristic electrostimulation intensity relationship corresponds to at least one symptom of the focal dystonia.

* * * * *